US00PP29825P2

(12) United States Plant Patent
Westervelt

(10) Patent No.: US PP29,825 P2
(45) Date of Patent: Nov. 13, 2018

(54) WHITE SPRUCE TREE NAMED 'WESTERVELT'

(50) Latin Name: *Picea glauca*
Varietal Denomination: Westervelt

(71) Applicant: Keith Westervelt, Manhattan, KS (US)

(72) Inventor: Keith Westervelt, Manhattan, KS (US)

(73) Assignee: BLUEVILLE NURSERY, INC., Manhattan, KS (US)

( * ) Notice: Subject to any disclaimer, the term of this patent is extended or adjusted under 35 U.S.C. 154(b) by 0 days.

(21) Appl. No.: 15/530,340

(22) Filed: Dec. 27, 2016

(51) Int. Cl.
*A01H 7/00* (2006.01)

(52) U.S. Cl.
USPC ..... Plt./213

(58) Field of Classification Search
USPC ..... Plt./213
See application file for complete search history.

*Primary Examiner* — Susan McCormick Ewoldt
(74) *Attorney, Agent, or Firm* — Penny J. Aguirre

(57) ABSTRACT

A new cultivar of white spruce tree named 'Westervelt' characterized by its needle foliage that is blue in color and soft in texture, needles and foliage that is narrow in diameter and size and upright and narrow plant habit with a strong central leader.

2 Drawing Sheets

Botanical classification: *Picea glauca.*
Varietal denomination: 'Westervelt'.

BACKGROUND OF THE INVENTION

The present invention relates to a new and distinct cultivar of *Picea* and will be referred to hereafter by its cultivar name, 'Westervelt'. 'Westervelt' represents a new cultivar of black hills spruce, an evergreen plant grown for landscape use.

The inventor discovered 'Westervelt' as a chance seedling in February of 2002 that was growing in a row of unnamed plants of *Picea glauca* that had been lined out in a field plot at his nursery in Manhattan, Kans. The parent plants are therefore unknown.

Asexual propagation of the new cultivar was first accomplished by grafting in Dayton, Oreg. in February of 2006 under the direction of the Inventor. Asexual propagation by grafting has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Westervelt' as a unique cultivar of *Picea.*

1. 'Westervelt' exhibits needle foliage that is blue in color.
2. 'Westervelt' exhibits needle foliage that is soft in texture.
3. 'Westervelt' exhibits an upright and narrow plant habit with a strong central leader.

The unnamed plants of *Picea glauca* growing in the area of discovery differ from 'Westervelt' in having foliage that is more green in color and less soft in texture, and a plant habit that is less narrow. 'Westervelt' can be most closely compared to the cultivars 'Blue Wonder' (U.S. Plant Pat. No. 10,933) and 'Cupressina' (not patented). 'Blue Wonder' is similar to 'Westervelt' in having blue foliage but differs from 'Westervelt' in having foliage that is less soft and in having a more compact and less narrow plant habit. 'Cupressina' is similar to 'Westervelt' in having a narrow plant habit but differs from 'Westervelt' in having dark green foliage.

BRIEF DESCRIPTION OF THE DRAWINGS

The plant and plant parts depicted in the accompanied photographs illustrate the characteristics of 'Westervelt'. The photographs were taken of a ten year-old plant as grown in the ground in Manhattan, Kans.

Figure 1:
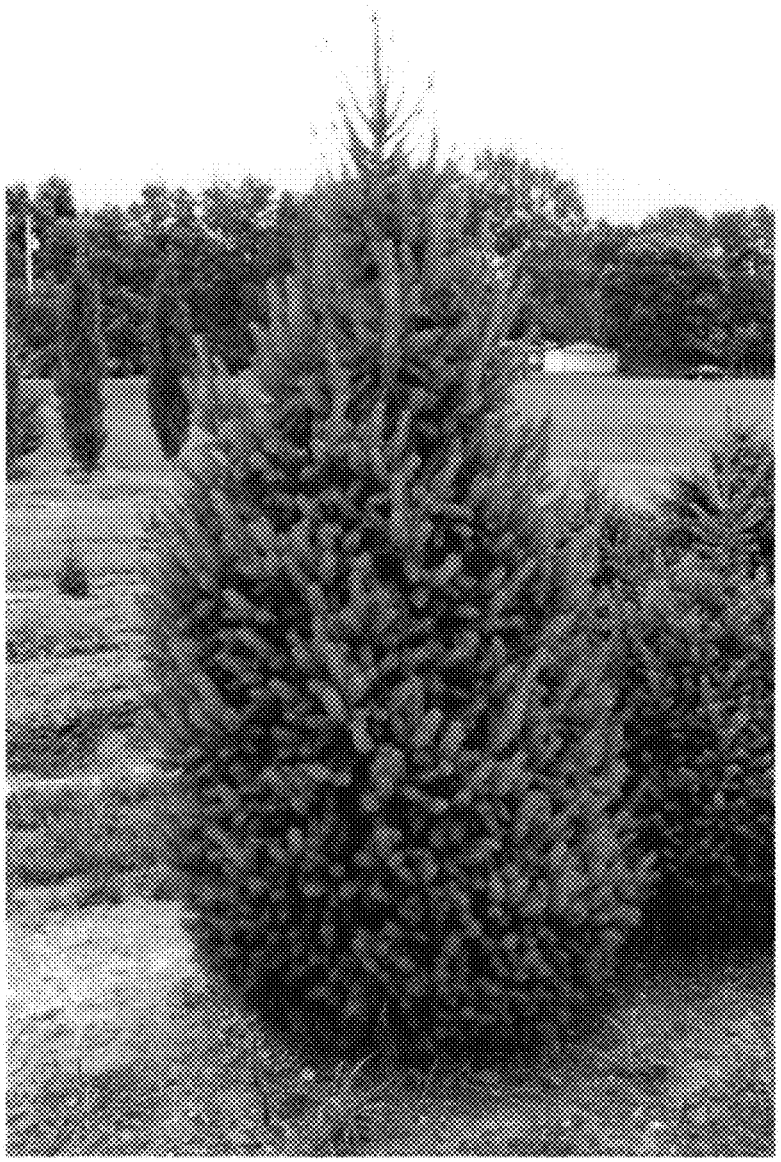
FIG. 1 provides an overall view of the plant habit of 'Westervelt'.
Figure 2:
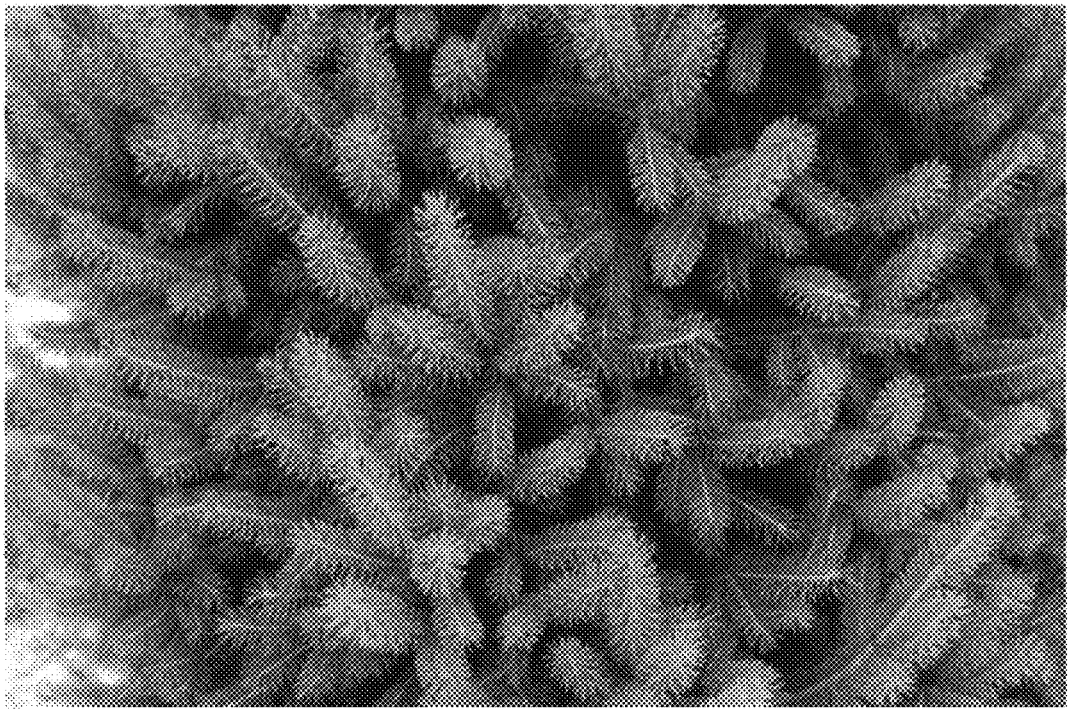
FIG. 2 provides a close-up view of the foliage 'Westervelt'.

The colors in the photographs are as close as possible with the photographic and printing technology utilized. The color values cited in the detailed botanical description accurately describe the colors of the new *Picea.*

DETAILED BOTANICAL DESCRIPTION

The following is a detailed description of the new cultivar as taken from 3 year-old trees as grown outdoors in 30-liter containers in Manhattan, Kans. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type.*—Coniferous, evergreen for landscape use.

*Growth habit.*—Narrowly upright.

*Height and spread.*—An average of 100 cm in height and 50 cm in width on a 3 year-old tree, a 14 year-old plant will reach 6 m in height with a spread of 0.7 to 1 m.

*Hardiness.*—At least in U.S.D.A. Zones 2 to 6.

*Diseases and pests.*—No susceptibility or resistance to pests or diseases has been observed.

*Root description.*—Fibrous, moderately branched, moderately thick, a blend of N199B and N199C in color.

*Growth rate.*—Slow, 15 to 20 cm per year.

*Propagation.*—Grafting.

*Time to produce a young plant.*—About 2 years to fully develop in a 2-gallon container starting from grafting onto understock of Norway spruce in the winter.

Branch description:

*Trunk and branch shape.*—Rounded.

*Branch size.*—Main trunk; 100 cm in length, 3 cm in diameter measured 2 cm from soil level, lateral branches; average of 55 cm in length, up to 1.5 cm in width, tertiary branches; up to 35 cm in length, 7 cm in width.

*Stem surface.*—Main and lateral branches; finely covered with bark, covered with lenticels, raised, 12 per 2×2 cm, 200A in color.

*Branching.*—Average of 14 lateral branches, 2 to 3 tertiary branches per lateral, strong central leader.

*Stem arrangement.*—Main branches; whorled, irregular, lateral branches; opposite.

*Stem aspect.*—Strong, held at an average angle of 45° or less.

*Internode length.*—Average of 4 cm.

*Stem color.*—One year-old stems; 161C, mature bark; close to N199B, but lighter.

*Resin glands.*—None observed.

Foliage description:

*Leaf arrangement.*—Densely whorled needles.

*Leaf attachment.*—Sessile.

*Leaf shape.*—Linear, scale-like, obliquely pointed.

*Leaf division.*—Simple.

*Leaf base.*—Truncate.

*Leaf apex.*—Oblique.

*Leaf venation.*—Not visible.

*Leaf margins.*—Entire.

*Leaf fragrance.*—When crushed, it produces a pine-like fragrance.

*Leaf surface.*—Upper and lower surfaces; smooth, glossy.

*Leaf color.*—Immature and mature upper and lower surfaces; closest to 117C (189A on inner shaded leaves).

*Leaf texture.*—Finer than is typical for *Picea glauca.*

*Leaf size.*—An average of 2 cm in length and 0.8 mm in width.

*Leaf quantity.*—Average of 160 per branchlet 14 cm in length.

*Leaf buds.*—5 mm in length and 3 mm in width, a blend of 165A and 165B in color, comprised of imbricate scales orbicular and cupped in shape and average of 2 mm in length and width.

Cone description: Although cones have been observed in the past on the original tree, cones have not been observed on the plants available for data collection.

It is claimed:

1. A new and distinct cultivar of white spruce tree named 'Westervelt' as herein illustrated and described.

* * * * *